(12) United States Patent
Ley et al.

(10) Patent No.: US 7,951,187 B2
(45) Date of Patent: *May 31, 2011

(54) STENT CONFIGURATIONS

(75) Inventors: Timothy J. Ley, Shoreview, MN (US);
Graig L. Kveen, Maple Grove, MN (US); Timothy G.J. Ehr, Elk River, MN (US); Brian J. Brown, Hanover, MN (US); David L. Friesen, Otsego, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 545 days.

This patent is subject to a terminal disclaimer.

(21) Appl. No.: 12/036,559

(22) Filed: Feb. 25, 2008

(65) Prior Publication Data

US 2008/0167706 A1 Jul. 10, 2008

Related U.S. Application Data

(63) Continuation of application No. 10/160,494, filed on May 31, 2002, now Pat. No. 7,335,225, which is a continuation of application No. 09/316,827, filed on May 21, 1999, now Pat. No. 6,416,538, which is a continuation of application No. 08/947,620, filed on Oct. 9, 1997, now Pat. No. 6,013,091.

(51) Int. Cl.
*A61F 2/06* (2006.01)

(52) U.S. Cl. ..................................... 623/1.15

(58) Field of Classification Search ............... 623/1.15, 623/1.16, 1.17, 1.2; 606/191–198
See application file for complete search history.

(56) References Cited

U.S. PATENT DOCUMENTS

| 5,102,417 | A | 4/1992 | Palmaz |
| 5,449,373 | A | 9/1995 | Pinchasik et al. |
| 5,514,154 | A | 5/1996 | Lau et al. |
| 5,569,295 | A | 10/1996 | Lam |
| 5,591,197 | A | 1/1997 | Orth et al. |
| 5,603,721 | A | 2/1997 | Lau et al. |
| 5,630,829 | A | 5/1997 | Lauterjung |
| 5,653,727 | A | 8/1997 | Wiktor |
| 5,669,932 | A | 9/1997 | Fischell et al. |
| 5,695,516 | A | 12/1997 | Fischell et al. |
| 5,697,971 | A | 12/1997 | Fischell et al. |
| 5,716,396 | A | 2/1998 | Williams, Jr. |
| 5,718,713 | A | 2/1998 | Frantzen |
| 5,733,303 | A | 3/1998 | Israel et al. |
| 5,741,327 | A | 4/1998 | Frantzen |
| 5,755,776 | A | 5/1998 | Al-Saadon |
| 5,776,161 | A | 7/1998 | Globerman |
| 5,810,872 | A | 9/1998 | Kanesaka et al. |
| 5,827,321 | A | 10/1998 | Roubin et al. |
| 5,861,027 | A | 1/1999 | Trapp |
| 5,876,449 | A | 3/1999 | Starck et al. |
| 5,895,406 | A | 4/1999 | Gray et al. |
| 5,922,021 | A | 7/1999 | Jang |
| 5,935,162 | A | 8/1999 | Dang |

(Continued)

FOREIGN PATENT DOCUMENTS

DE 29615969 U1 10/1996

(Continued)

*Primary Examiner* — Kevin T Truong
(74) *Attorney, Agent, or Firm* — Vidas, Arrett & Steinkraus, P.A.

(57) ABSTRACT

Improved stent configurations exhibiting limited recoil, resistance to compression and improved longitudinal flexibility.

22 Claims, 12 Drawing Sheets

U.S. PATENT DOCUMENTS

| | | |
|---|---|---|
| 6,013,091 A | 1/2000 | Ley et al. |
| 6,053,940 A | 4/2000 | Wijay |
| 6,117,165 A | 9/2000 | Becker |
| 6,203,569 B1 | 3/2001 | Wijay |
| 6,270,524 B1 | 8/2001 | Kim |
| 6,348,065 B1 | 2/2002 | Brown et al. |
| 6,416,538 B1 | 7/2002 | Ley et al. |
| 7,655,032 B2 * | 2/2010 | Ley et al. .................. 623/1.15 |
| 7,740,654 B2 * | 6/2010 | Kveen et al. ............... 623/1.15 |
| 2002/0111669 A1 | 8/2002 | Pazienza et al. |
| 2004/0093058 A1 | 5/2004 | Cottone et al. |
| 2004/0093073 A1 | 5/2004 | Lowe et al. |
| 2005/0090894 A1 | 4/2005 | Pazienza et al. |
| 2005/0107865 A1 | 5/2005 | Clifford et al. |

FOREIGN PATENT DOCUMENTS

| | | |
|---|---|---|
| DE | 29701758 U1 | 3/1997 |
| DE | 29702671 U1 | 4/1997 |
| DE | 29708689 U1 | 7/1997 |
| DE | 29708879 U1 | 7/1997 |
| DE | 29716476 | 12/1997 |
| DE | 29805761 | 8/1998 |
| JP | 10155915 | 6/1998 |
| JP | 10165513 | 6/1998 |
| JP | 10201856 | 3/2008 |
| WO | 9509584 | 4/1995 |
| WO | 9603092 A1 | 2/1996 |
| WO | 9704721 | 2/1997 |
| WO | 9725937 | 7/1997 |
| WO | 9726840 | 7/1997 |
| WO | 9732543 | 9/1997 |
| WO | 9732544 | 9/1997 |
| WO | 9733534 | 9/1997 |
| WO | 9818405 | 5/1998 |
| WO | 9818406 | 3/2008 |

* cited by examiner

STENT CONFIGURATIONS

CROSS-REFERENCE TO RELATED APPLICATIONS

This application is a Continuation Application of U.S. application Ser. No. 10/160,494, filed May 31, 2002 which is a Continuation Application of U.S. application Ser. No. 09/316,827, filed May 21, 1999, issued as U.S. Pat. No. 6,416,538 which is a Continuation Application of U.S. application Ser. No. 08/947,620, filed Oct. 9, 1997, issued as U.S. Pat. No. 6,013,091, the entire contents of which are hereby incorporated by their reference.

BACKGROUND OF THE INVENTION

1. Field of the Invention

This invention relates to stents of improved configuration.

2. Brief Description of the Prior Art

Stents are radially expandable endoprosthesis which are typically intravascular implants capable of being implanted transluminally and enlarged radially after being introduced percutaneously. They have also been implanted in urinary tracts and bile ducts. They are used to reinforce body vessels and to prevent restenosis following angioplasty in the vascular system. They may be self-expanding or expanded by an internal radial force, such as when mounted on a balloon.

In the past, stents have been generally tubular but have been composed of many configurations and have been made of many materials, including metals and plastic. Ordinary metals such as stainless steel have been used as have shape memory metals such as Nitinol and the like. Stents have also been made of biodegradable plastic materials. Such stents have been formed from wire, tube stock, etc.

SUMMARY OF THE INVENTION

This invention provides new configurations of the cells making up stents which may be adapted to all of the various types of prior art stents described above and/or known previously in the art. There are numerous advantages to the new configurations. The configurations of the invention limit recoil and add resistance to compression for an expanded stent, among other things. Other configurations than cylindrical are contemplated, e.g., square, triangular octagonal, etc. The stents of this invention are longitudinally flexible and expandable.

BRIEF DESCRIPTION OF THE FIGURES

FIG. 5 is another stent embodiment of the invention similar in view to

FIG. 1 showing the flat plan of the stent in the unexpanded configuration;

DETAILED DESCRIPTION OF THE PREFERRED EMBODIMENTS

Figure 1:
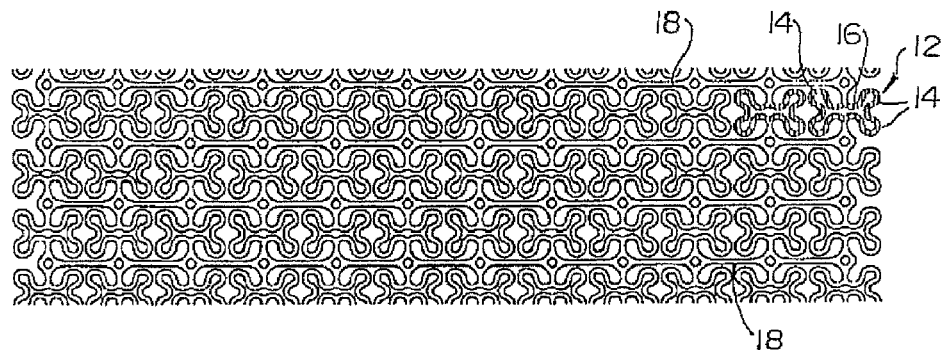
FIG. 1 is a flat plan view of an embodiment of the stent configuration of the invention in the unexpanded condition.
Figure 2:
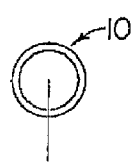
FIG. 2 is an end view of a stent of FIG. 1 according to the invention in its normal tubular unexpanded condition.
Figure 3:
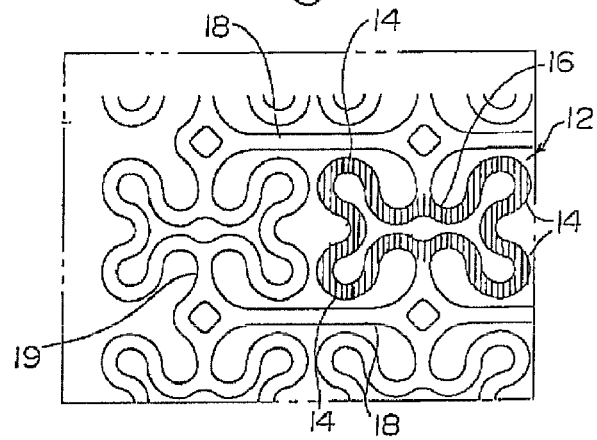
FIG. 3 is a detail view of a portion of FIG. 1, as indicated.
Figure 4:
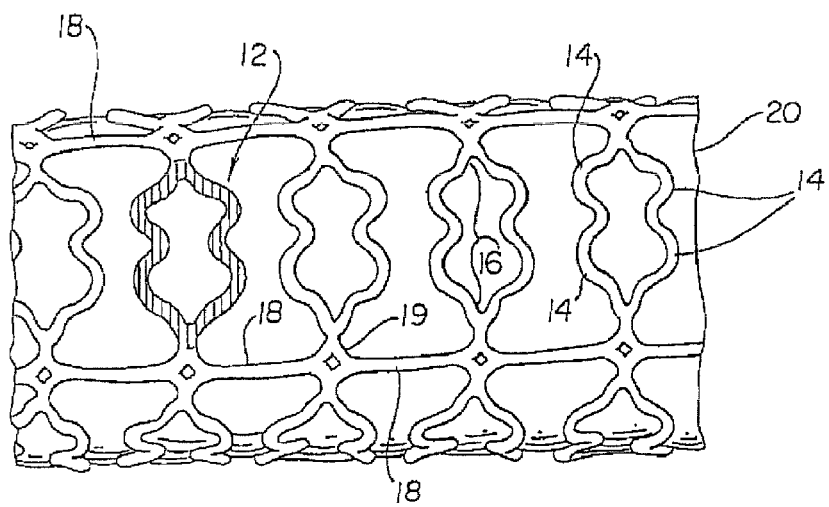
FIG. 4 is a view of the stent of FIGS. 1 and 2 expanded on a balloon.
Figure 1A:
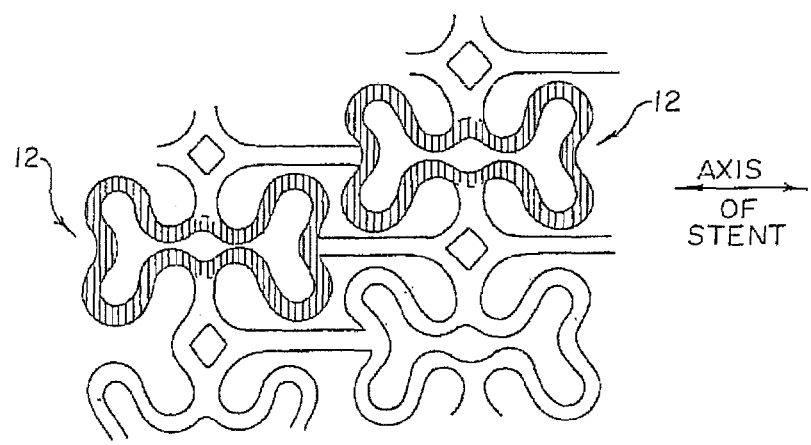
FIG. 1a is a fragmentary plan similar to FIG. 1 showing a staggered arrangement of the cells making up a stent.
Figure 1B:
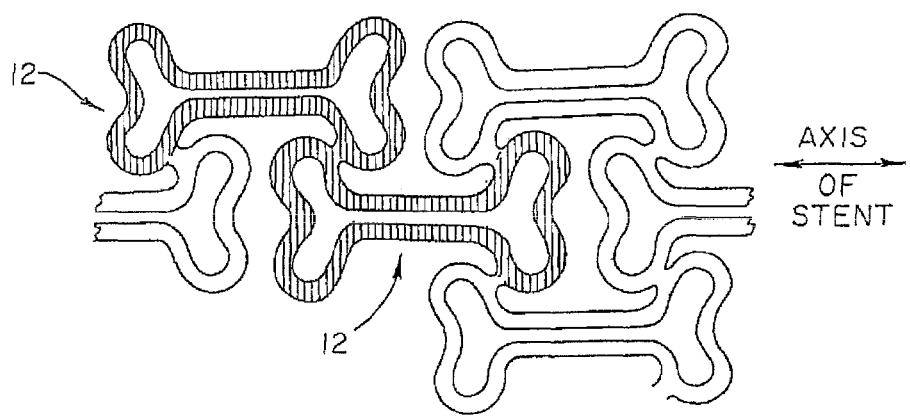
FIGS. 1b and 1c show cells similar to FIGS. 1 and 1a in different arrangements and with differing interconnection.
Figure 1C:
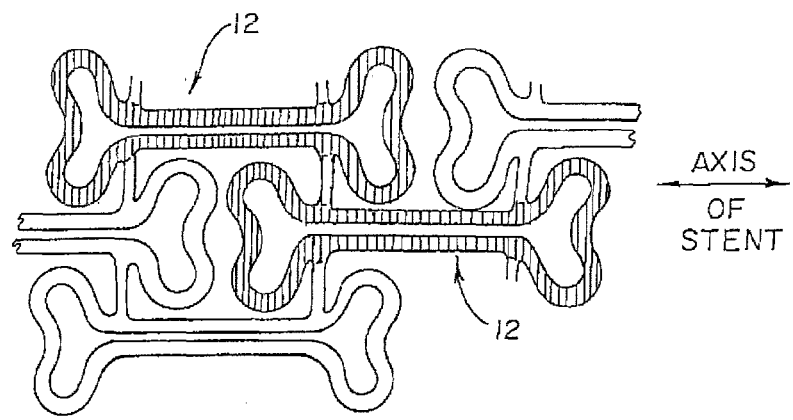

A preferred embodiment of a generally cylindrical stent 10 according to the invention is illustrated in FIGS. 1-4. It comprises a metal tube as shown in FIGS. 2 and 4, such as nitinol or stainless steel preferably, which has been etched or preferably laser cut to the configuration shown in the flat plan view of FIG. 1. An enlarged detail of FIG. 1 is shown in FIG. 3. The configuration is made up of a series of curvilinear expansion cell elements generally indicated at 12 (see darkened example in FIG. 3 for clarity) having relatively wide end portions 14 joined by relatively narrow center portions 16. Cells 12 are arranged longitudinally as shown in FIG. 1 end to end with respect to the longitudinal axis of the stent 10 and in substantially parallel rows as also shown in FIG. 1. A plurality of longitudinally extending elongate support members 18 are included, one each being disposed between adjacent rows of cells 12. Also, a plurality of circumferentially extending support members 19, preferably substantially normal to support members 18 are also positioned between the rows of cells 12 to intersect portions of the support members 18 and to interconnect them to the narrow center portions 16 of cells 12. As can be seen in FIG. 1a, cells 12 may also be arranged in a staggered arrangement. FIGS. 1b and 1c demonstrate different arrangements and interconnections for cells 12.

When the stent is expanded, as shown in FIG. 4, on a balloon 20 the cells 12 take on a new configuration as shown, the members making up the stent being indicated by the same numbers as used in FIG. 1 and FIG. 3. Again, one cell is shown darkened for clarity.

Figure 5:
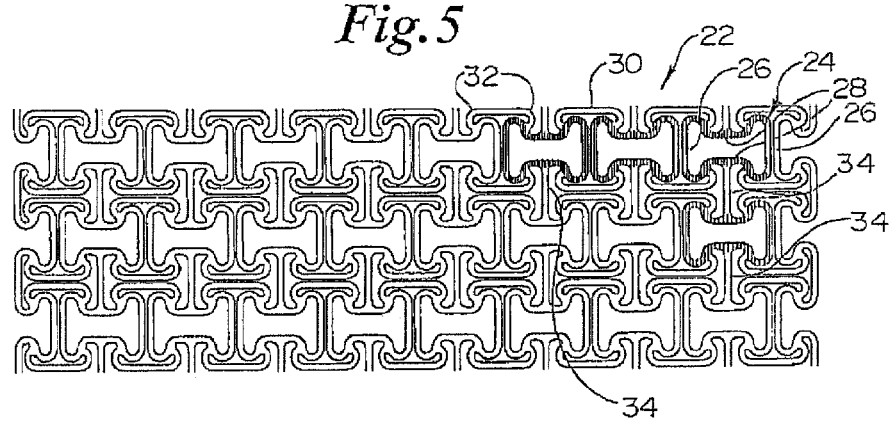
Figure 6:
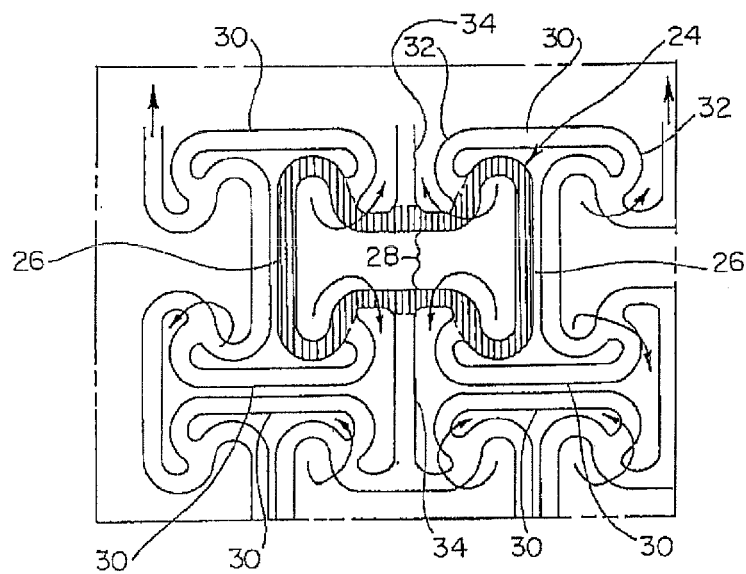
FIG. 6 is a detail view of a portion of FIG. 5, as indicated.
Figure 7:
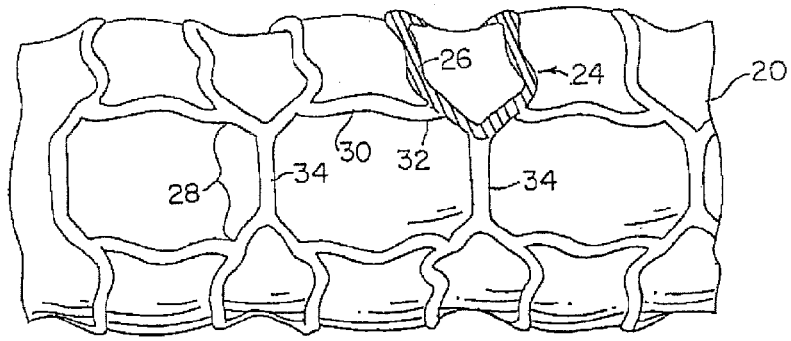
FIG. 7 is a showing of the stent of FIG. 4 expanded on a balloon.

Referring now to FIGS. 5-7, another stent embodiment generally indicated at 22 of the invention is shown. In this embodiment, as seen in FIGS. 5 and 6, expansion cells 24, best seen in the detail of FIG. 6 and indicated by darkened portion, have relatively wide end portions 26, best seen in FIG. 6, and narrow center portions 28 and are arranged end to end in longitudinal rows as described with respect to the first embodiment. Adjacent end portions 26 are interconnected by pairs of longitudinal support members in the form of segments 30 which have curved end portions 32. Circumferential extending segments 34 extend between rows of cells 24 to interconnect the narrow center portions 28.

Upon radial expansion of the stent, as on a balloon 20 for example, its configuration changes by deformation force in the directions shown by the arrows in FIG. 6 to that configuration shown in FIG. 7. The elements indicated in FIG. 7 are identified by the same numbers indicated for similar elements in FIGS. 5 and 6.

Figure 20:
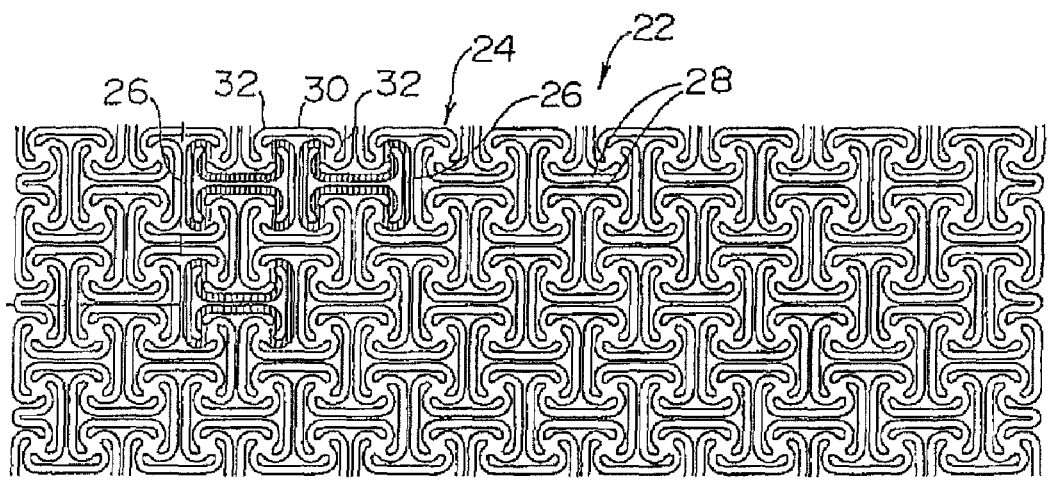
FIG. 20 is a flat plan view similar to FIGS. 1, 5, 8, 11, 15 and 18 showing yet another stent embodiment in the unexpanded condition.
Figure 21:
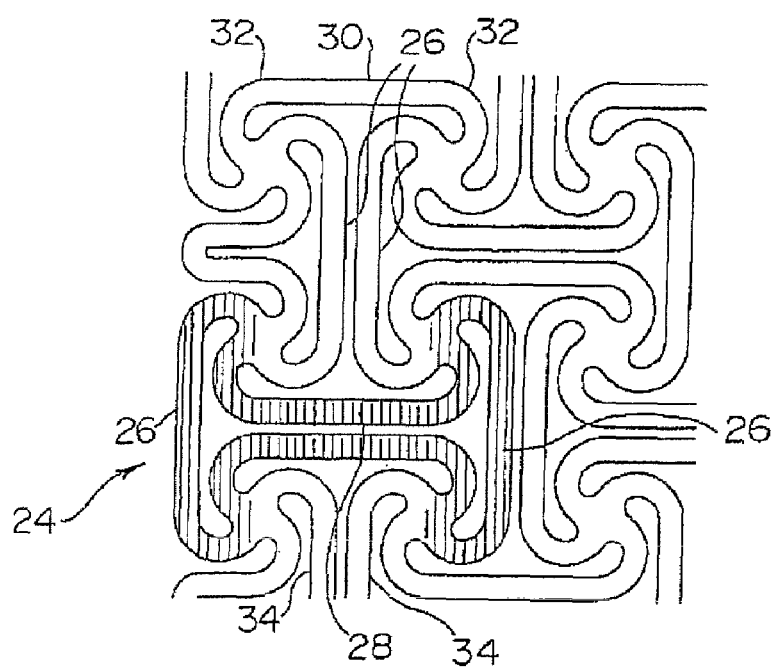
FIG. 21 is a detail view of a portion of FIG. 20.

FIGS. 20 and 21 show a configuration somewhat similar to that of FIGS. 5-7 but without interconnecting elements 28.

Figure 8:
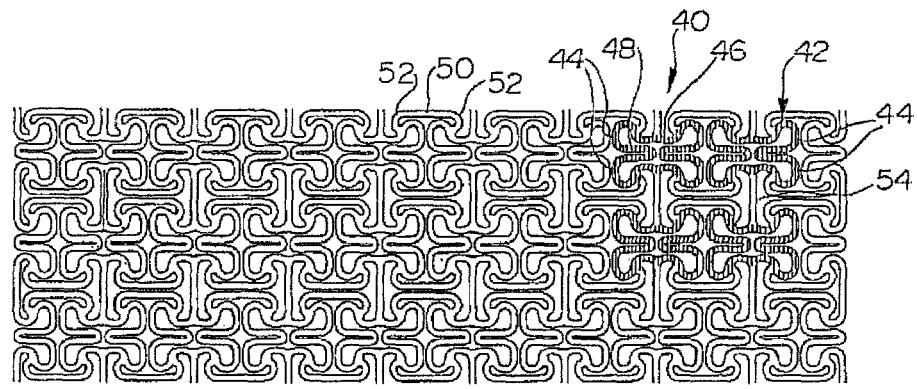
FIG. 8 is a flat plan similar to FIGS. 1 and 5 showing another stent embodiment in the unexpanded condition.
Figure 9:
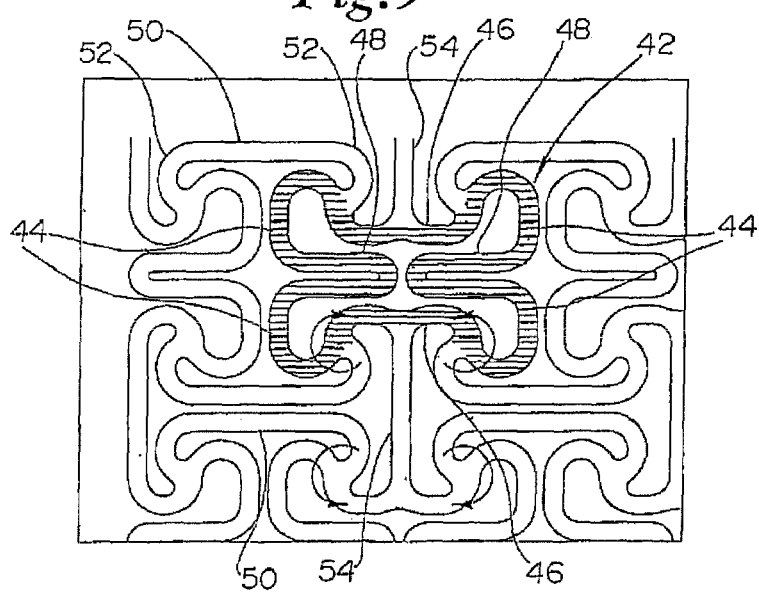
FIG. 9 is a detail view of a portion of FIG. 8, as indicated.
Figure 10:
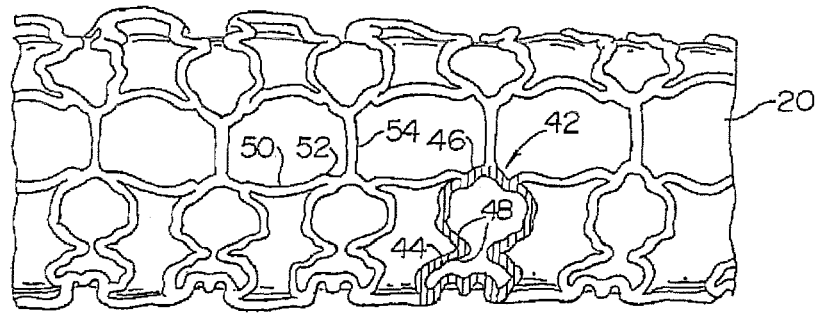
FIG. 10 is a showing of the stent of FIG. 8 expanded on a balloon.
Figure 8A:
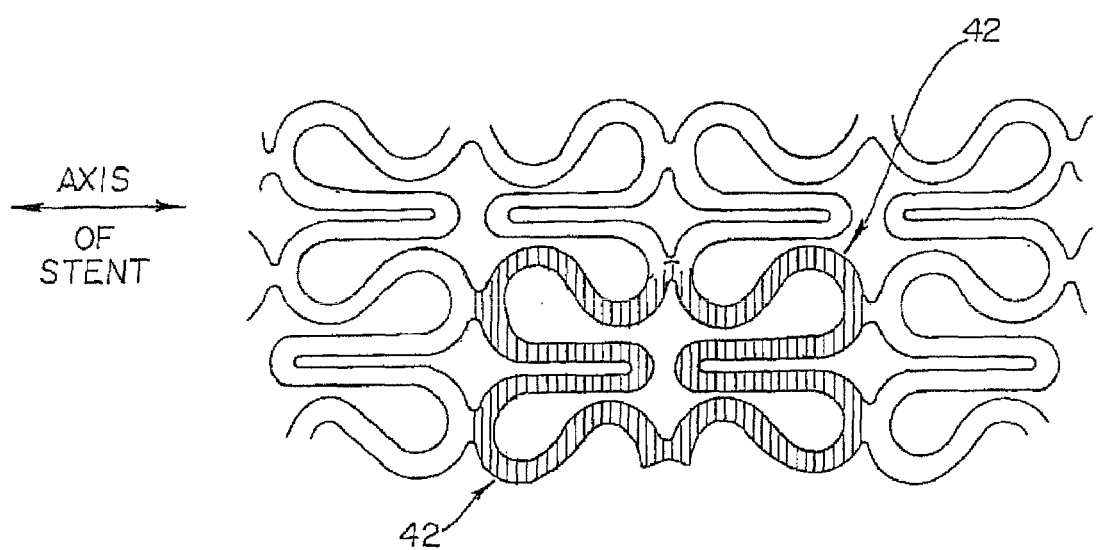
FIG. 8a is a plan view in fragment showing a variation of the cell configuration shown in FIG. 8.

Referring now to FIGS. 8-10, another stent embodiment of the invention is shown and generally indicated at 40. Again, as seen in FIGS. 8 and 9, expansion cells 42 (example darkened for clarity) have relatively wide end portions 44 and narrow center portions 46. The end portions include inwardly extending loop portions 48. Cells 42 are arranged end to end in longitudinal rows as in the preceding embodiments. Adjacent end portions 44 are interconnected by pairs of longitudinal support member segments 50 which have curved end portions 52. Circumferentially extending segments 54 extend between rows of cells 42 to interconnect the narrow center portions 46 of the cells. FIG. 8a shows a variation in shape for cells 42.

Upon radial expansion of the stent upon a balloon 20, the configuration changes to that shown in FIG. 10. The arrows show the direction of force of deformation upon expansion.

Figure 11:
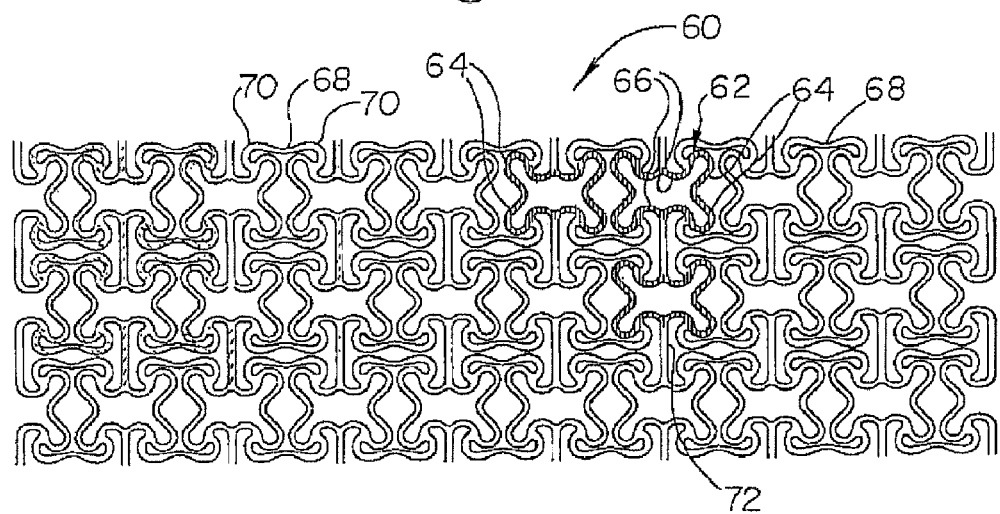
FIG. 11 is a flat plan similar to FIGS. 1, 5, and 8 showing yet another stent embodiment in the unexpanded condition.
Figure 12:
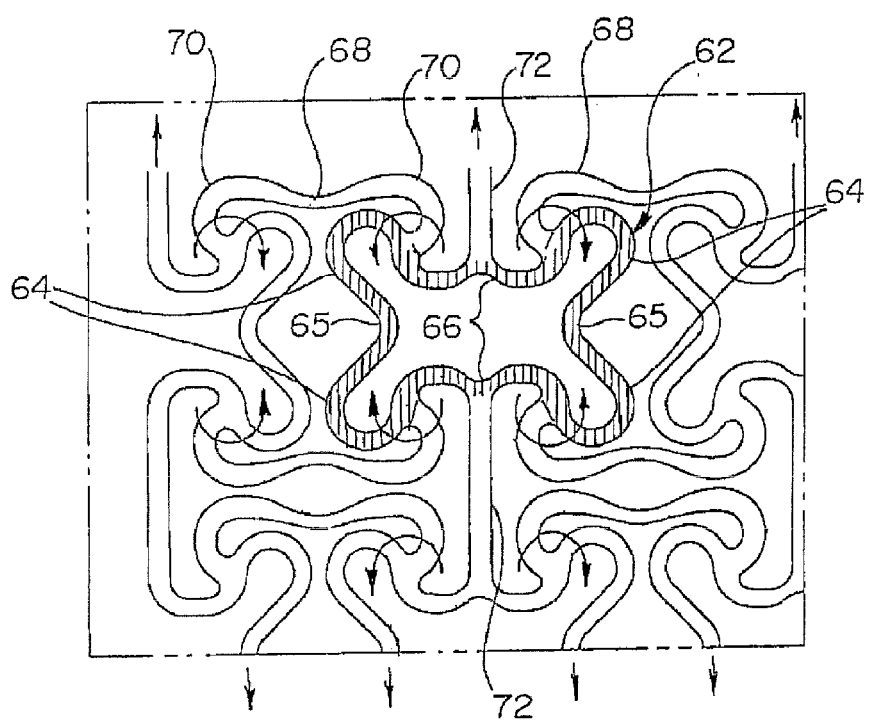
FIG. 12 is a detail view of a portion of FIG. 11, as indicated.

Referring now to FIGS. 11 and 12, still another embodiment of a stent 60 is shown. Again, as shown in FIGS. 11 and 12, expansion cells 62 (example darkened for clarity) have relatively wide end portions 64 having a slight inward bend 65 to them and narrow center portions 66. Cells 62 are arranged end to end in longitudinal rows as in the preceding embodiments. Adjacent end portions 64 are interconnected by pairs of longitudinal support member segments 68 which have curved end portions 70. Circumferentially extending segments 72 extend between rows of cells 62 to interconnect the narrow center portions 66 of the cells.

Figure 13:
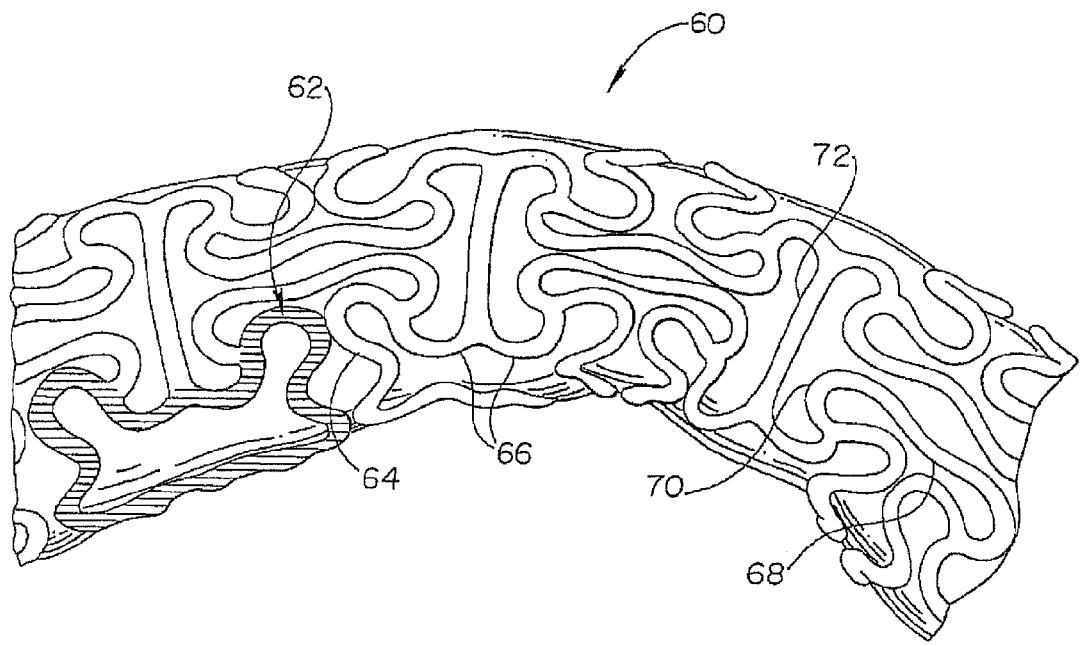
FIG. 13 is a view of the stent of FIG. 11 on an unexpanded balloon demonstrating its flexibility in the unexpanded condition.

Reference to FIG. 13 will show the inherent flexibility of the stents of this invention.

Figure 14:
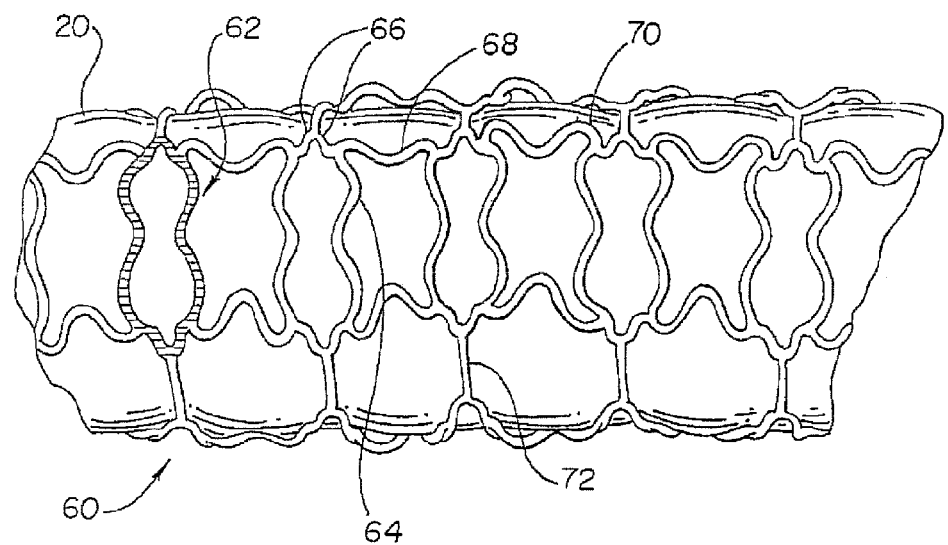
FIG. 14 is a showing of the stent of FIG. 11 expanded on a balloon.

Upon radial expansion of the stent upon a balloon 20, the configuration changes to that shown in FIG. 14.

Figure 15:
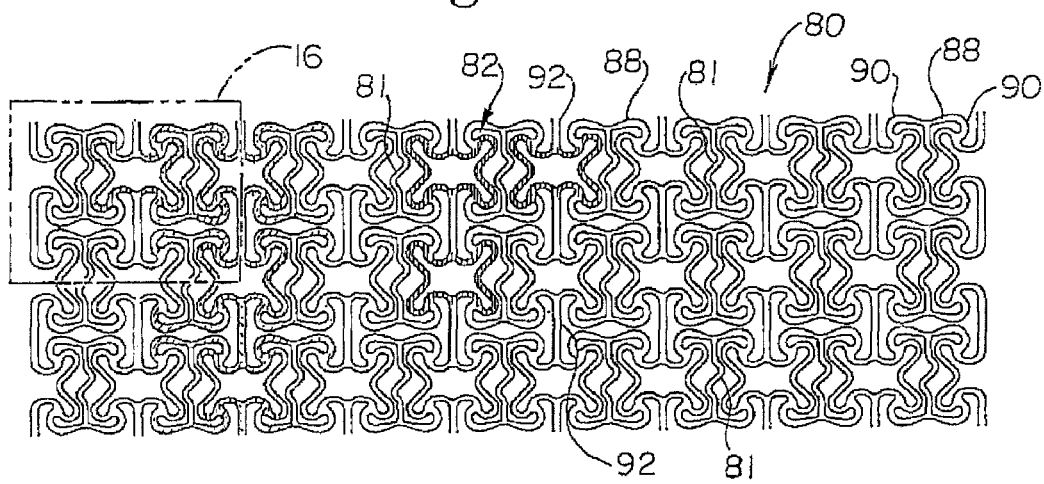
FIG. 15 is a flat plan similar to FIGS. 1, 5, 8, and 11 showing yet another stent embodiment in the unexpanded condition.
Figure 16:
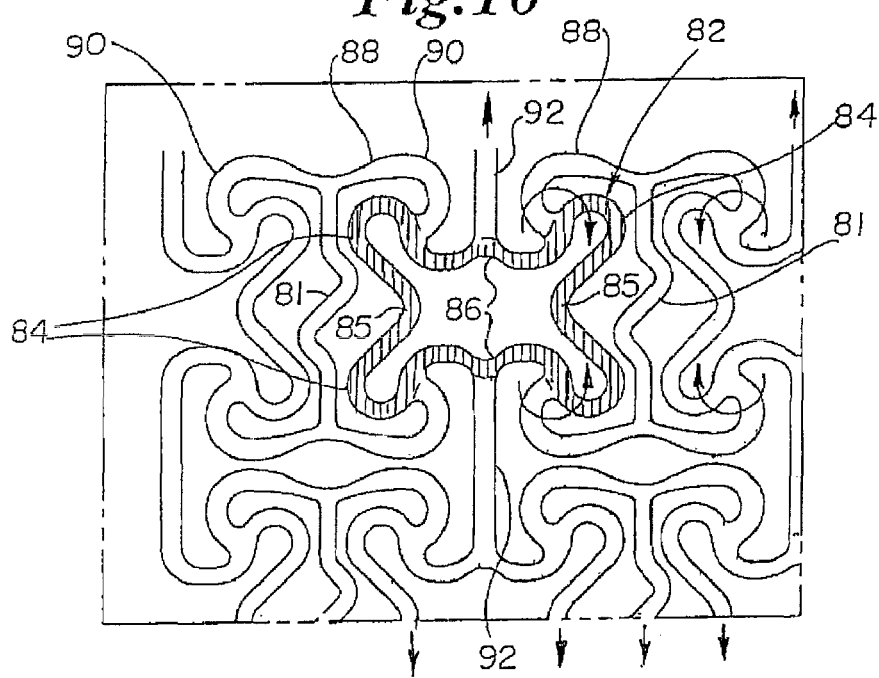
FIG. 16 is a detail view of a portion of FIG. 15, as indicated.

Referring now to FIGS. 15 and 16, yet another embodiment of a stent 80 is shown in a configuration quite similar to that of FIGS. 11-14 but with an added circumferentially extending structural element 81. Again, as best seen in FIG. 16, expansion cells 82 (examples darkened for clarity) have relatively wide end portions 84 having a slight inward bend 85 to them and narrow center portions 86. Cells 82 are arranged end to end in longitudinal rows as in the preceding embodiments. Adjacent end portions 84 are interconnected by pairs of longitudinal support member segments 88 which have curved end portions 90. Circumferentially extending segments 92 extend between rows of cells 82 to interconnect the narrow center portions 86 of the cells. Circumferentially extending segments 81 interconnect pairs of support member segments 88.

Figure 17:
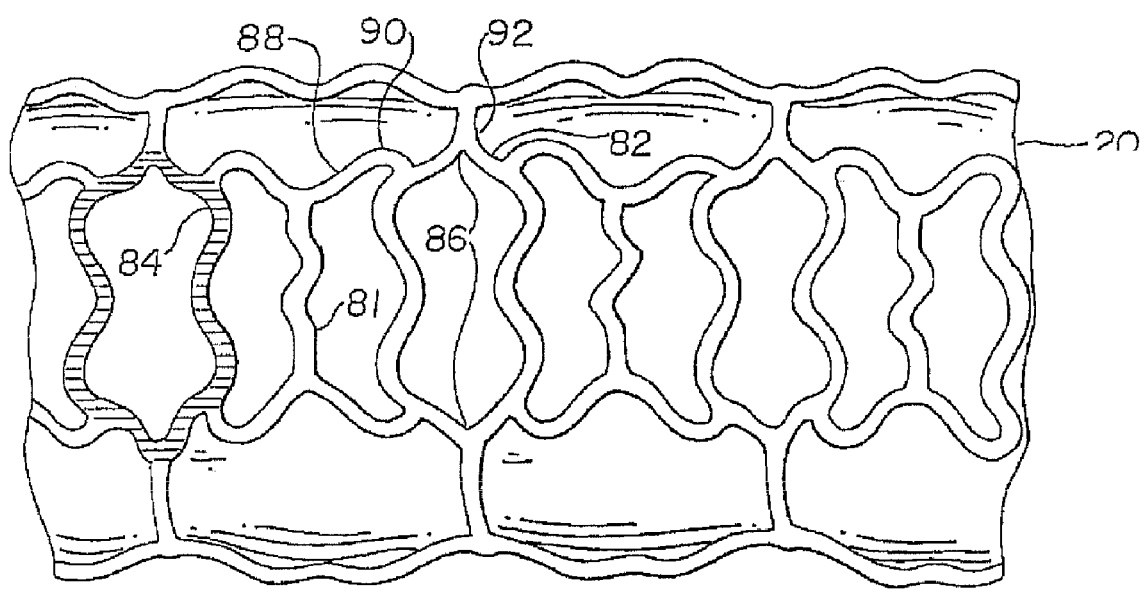
FIG. 17 is a showing of the stent of FIG. 15 expanded on a balloon.

Upon radial expansion of the stent on a balloon 20, the configuration changes to that shown in FIG. 17.

Figure 18:
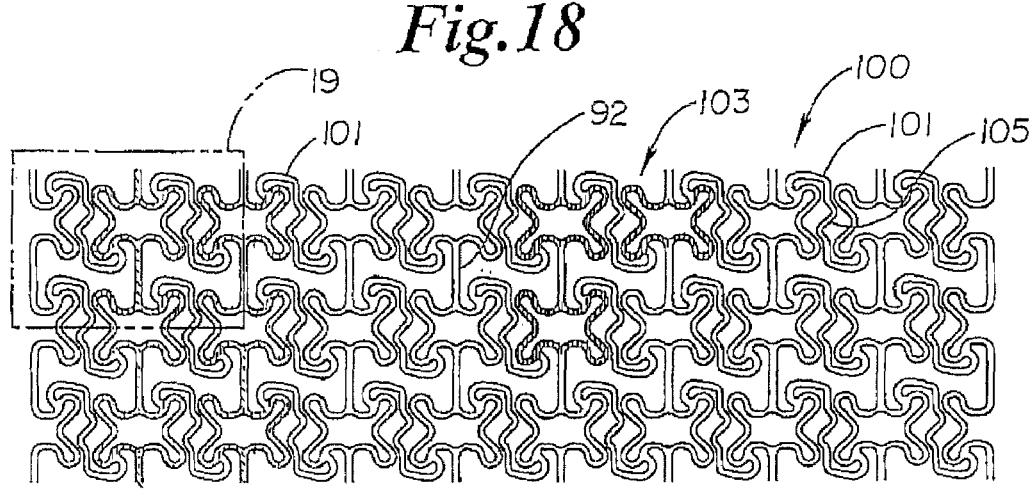
FIG. 18 is a flat plan similar to FIGS. 1, 5, 8, 11 and 15 showing still another stent embodiment in the unexpanded condition.
Figure 19:
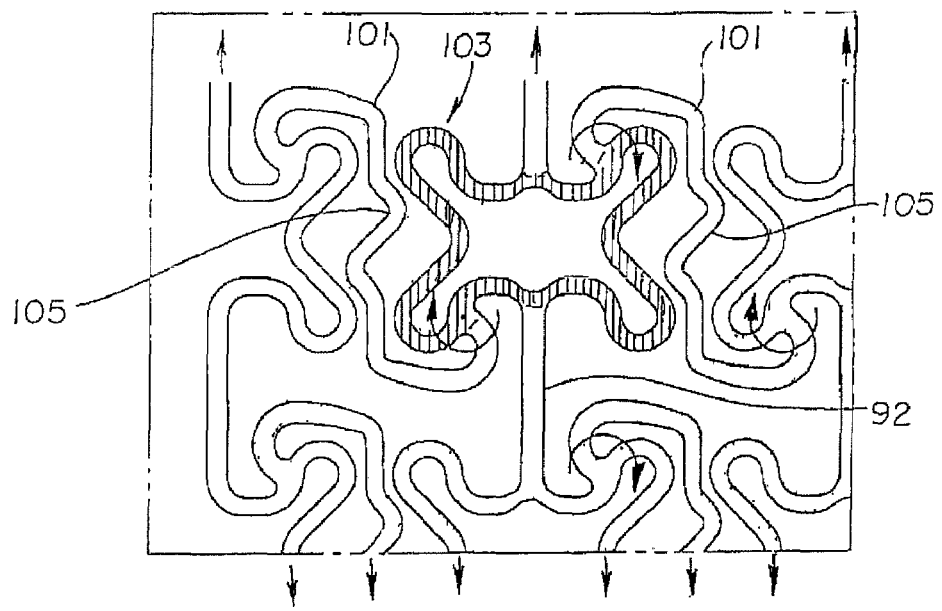
FIG. 19 is a detail view of a portion of FIG. 18, as indicated.

Referring now to FIGS. 18 and 19, still another embodiment of a stent configuration 100 is shown. As before this embodiment is similar to that of FIGS. 11-12 except that the circumferentially extending segments 101 are arranged differently than those identified in FIGS. 11-12 as 72. In this embodiment the circumferentially extending members 101 extend between the adjacent ends of adjacent cells 103 (examples darkened for clarity) to interconnect the top of one end to the bottom of the adjacent end and the members 101 have a slight curve or bend 105 in their length. The other members are all similarly numbered as in the preceding Figures.

Figure 22:
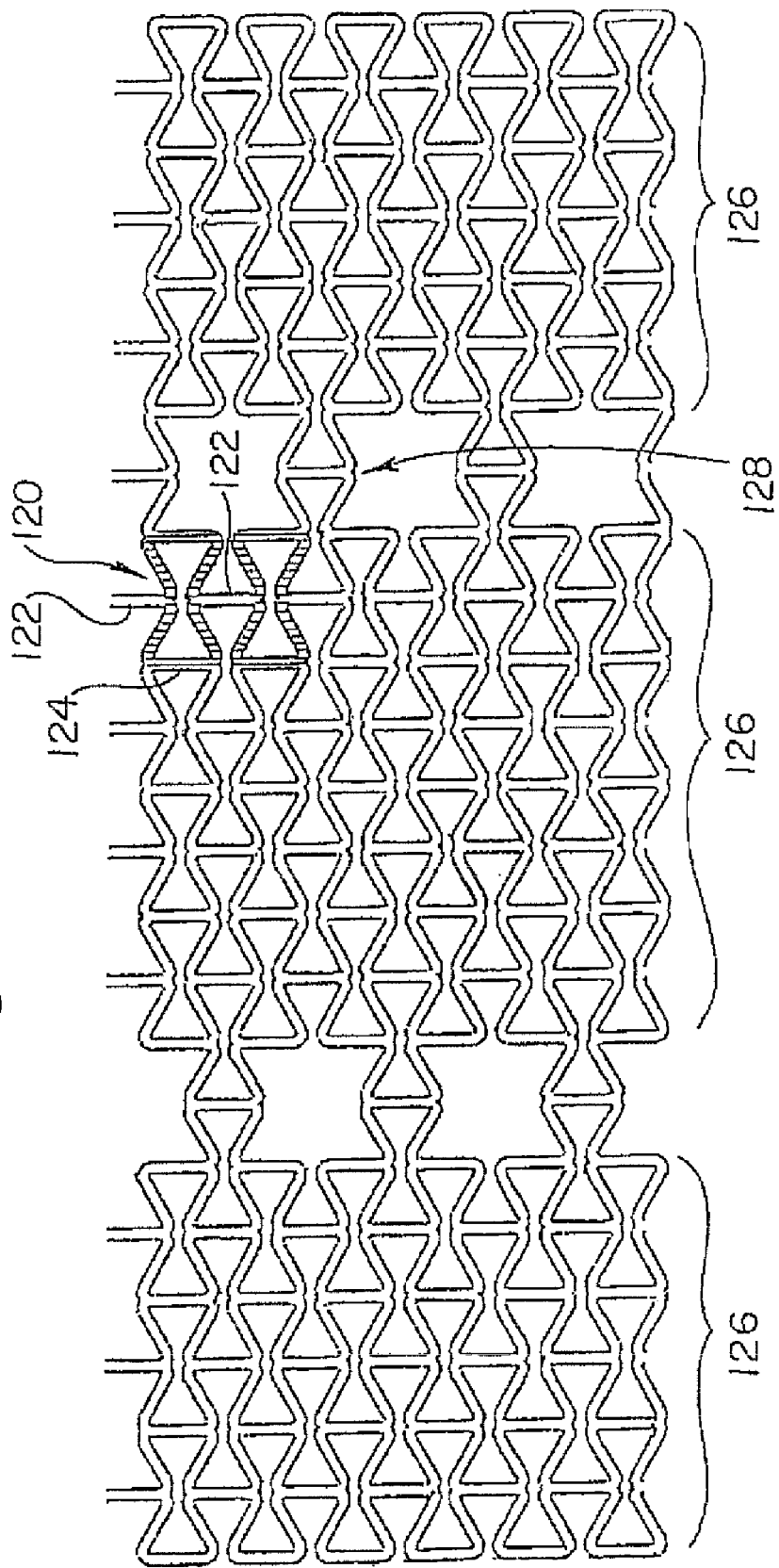
FIG. 22 is a flat plan view of another embodiment of the invention.

FIG. 22 shows yet another embodiment of a stent comprised of cells 120 having interconnecting circumferential extending members 122. The cells have common sides or end members 124 and are arranged in groups to form bands 126 which are interconnected by joined cells 128.

While this invention may be embodied in many different forms, there are described in detail herein specific preferred embodiments of the invention. This description is an exemplification of the principles of the invention and is not intended to limit the invention to the particular embodiments illustrated.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A stent of generally cylindrical shape comprising a plurality of interconnected cells having relatively wide end portions joined by a narrow center portion, the cells arranged end to end, longitudinally in longitudinal rows with respect to the longitudinal axis of the stent, characterized in that longitudinally adjacent cells are engaged by pairs of longitudinal support members having curved end portions.

2. The stent of claim 1 wherein each cell having relatively wide end portions joined by a narrow center portion is connected to an adjacent such cell via a straight, circumferentially extending connector.

3. The stent of claim 1, the plurality of interconnected cells forming helically extending bands of cells having relatively wide end portions joined by a narrow center portion.

4. The stent of claim 1, the plurality of interconnected cells including cells having a longitudinal axis parallel to the longitudinal axis of the stent.

5. The stent of claim 1, the plurality of interconnected cells including cells having a longitudinal axis perpendicular to the longitudinal axis of the stent.

6. The stent of claim 1 the plurality of interconnected cells including cells having a longitudinal axis perpendicular to the longitudinal axis of the stent and cells having a longitudinal axis parallel to the longitudinal axis of the stent.

7. The stent of claim 1, the relatively wide end portions having inwardly extending loop portions.

8. The stent of claim 1, the relatively wide end portions having a slight inward bend.

9. The stent of claim 2, the stent further comprising a plurality of circumferentially extending segments interconnecting pairs of longitudinal support members.

10. The stent of claim 9, the plurality of interconnected cells including first cells having a longitudinal axis parallel to the longitudinal axis of the stent and second cells having a longitudinal axis parallel to the longitudinal axis of the stent, the first cells having a first shape, the second cells having a second shape, the first shape different than the second shape.

11. The stent of claim 2, the straight, circumferentially extending connector interconnecting the narrow center portion of the cells.

12. The stent of claim 1, the plurality of interconnected cells including first cells having a longitudinal axis parallel to the longitudinal axis of the stent and second cells having a longitudinal axis perpendicular to the longitudinal axis of the stent.

13. The stent of claim 12, the first cells having a first size and the second cells having a second size, the second size being smaller than the first size.

14. The stent of claim 13, the first cells having relatively wide end portions that are substantially straight and narrow center portions that are substantially straight, the second cells having relatively wide end portions that are longitudinal support members and narrow center portions that are the relatively wide end portions of the first cells.

15. The stent of claim 12, the interconnected cells further including third cells having a longitudinal axis parallel to the longitudinal axis of the stent, the first cells having a first shape, the second cells having a second shape, the third cells having a third shape, the first, second and third shapes being different.

16. The stent of claim 15, the first cells having relatively wide end portions with a slight inward bend, the second cells having relatively wide end portions that are the longitudinal support member segments and relatively narrow center portions that are the relatively wide end portions with a slight inward bend, the third cells having relatively wide end portions that are straight and relatively narrow center portions that are the longitudinal support member segments.

17. The stent of claim 15, the first cells having relatively wide end portions with inwardly extending loop portions, the second cells having relatively wide end portions that are substantially straight and relatively narrow center portions that have outwardly extending loop portions, the third cells having relatively wide end portions and relatively narrow center portions that are substantially straight.

18. The stent of claim 12, the first cells and the second cells having the same size and the same shape, adjacent longitudinal rows of first cells being longitudinally staggered and adjacent circumferential rows of second cells being circumferentially staggered.

19. A stent, the stent comprising
a plurality of cells having relatively wide end portions joined by a narrow center portion, the cells arranged end to end, longitudinally in longitudinal rows with respect to the longitudinal axis of the stent;
a plurality of first circumferentially extending segments, longitudinally adjacent cells being engaged by a first circumferentially extending segment; and
a plurality of second circumferentially extending segments, circumferentially adjacent cells being engaged by at least one second circumferentially extending segment.

20. The stent of claim 19, each first circumferentially extending segment extending from a top portion to a bottom portion of longitudinally adjacent cells.

21. The stent of claim 20, each first circumferentially extending segment having a plurality of turns.

22. The stent of claim 20, each second circumferentially extending segment being substantially straight.

* * * * *